(12) United States Patent
Qin et al.

(10) Patent No.: US 7,824,876 B2
(45) Date of Patent: Nov. 2, 2010

(54) METHOD FOR DIAGNOSING ACUTE CORONARY SYNDROME

(75) Inventors: Qiu-Ping Qin, Turku (FI); Kim Pettersson, Turku (FI)

(73) Assignee: Turun Yliopisto, Turun Yliopisto (FI)

( * ) Notice: Subject to any disclaimer, the term of this patent is extended or adjusted under 35 U.S.C. 154(b) by 747 days.

(21) Appl. No.: 10/580,329

(22) PCT Filed: Jan. 19, 2005

(86) PCT No.: PCT/FI2005/000036

§ 371 (c)(1),
(2), (4) Date: May 24, 2006

(87) PCT Pub. No.: WO2005/073727

PCT Pub. Date: Aug. 11, 2005

(65) Prior Publication Data

US 2007/0111254 A1 May 17, 2007

Related U.S. Application Data

(60) Provisional application No. 60/539,431, filed on Jan. 28, 2004.

(51) Int. Cl.
G01N 33/573 (2006.01)
G01N 33/536 (2006.01)
G01N 33/538 (2006.01)
G01N 33/543 (2006.01)

(52) U.S. Cl. .................. 435/7.4; 435/7.8; 435/7.92; 435/7.93; 435/7.94; 436/518; 436/536; 436/541; 436/175; 436/178; 530/388.25; 530/388.26; 530/389.1; 530/389.3; 530/391.1; 530/391.3

(58) Field of Classification Search .............. 435/7.4, 435/7.8, 7.92, 7.93, 7.94; 436/518, 536, 436/541, 175, 178; 530/388.25, 388.26, 530/389.1, 389.3, 391.1, 391.3
See application file for complete search history.

(56) References Cited

U.S. PATENT DOCUMENTS

| | | | |
|---|---|---|---|
| 4,225,574 A | 9/1980 | Romelli et al. ................. | 424/1 |
| 4,366,143 A | 12/1982 | Midgley et al. ............. | 436/501 |
| 6,500,630 B2 * | 12/2002 | Conover et al. ............ | 435/7.94 |
| 7,115,382 B1 * | 10/2006 | Overgaard et al. .......... | 435/7.4 |

FOREIGN PATENT DOCUMENTS

| | | |
|---|---|---|
| WO | WO 00/54806 | 9/2000 |
| WO | WO 02/056015 | 7/2002 |

OTHER PUBLICATIONS

Bayes-Genis et al., "Pregnancy-associated Plasma Protein A As A Marker of Acute Coronary Syndrome," 345 *N. Engl. J. Med.* 1022-29 (2001).

Qin et al., "Molecular Distinction of Circulating Pregnancy-Associated Plasma Protein A in Myocardial Infarction and Pregnancy," 51 *Clinical Chemistry* 75-83 (2005).
Lund et al., "Circulating Pregnancy-Associated Plasma Protein A Predicts Outcome in Patients with Acute Coronary Syndrome but No Troponin I Elevation," 108 *Circulation* 1924-1926 (2003).
Cosin-Sales et al., "PAPP-A, ProMBP, and PAPP-A/ProMBP Ratio are Related to the Extent of Anglographic Coronary Artery Disease in Stable Angina Patients," 41 *JACC Supplement A* 359A (Mar. 19, 2003).
Khosravi et al., "Pregnancy Associated Plasma Protein-A: Ultrasensitive Immunoassay and Determination in Coronary Heart Disease," 35 *Clinical Biochemistry* 531-538 (2002).
Qiu-Ping Qin, et al., "Point-of-Care Time-resolved Immunofluorometric Assay for Human Pregnancy-associated Plasma Protein A: Use in First-Trimester Screening for Down Syndrome," 48 *Clinical Chemistry* 473-483 (2002).
Arun S. Sivanandam, et al., "Studies on regulation of IGF (insulin-like growth factor)-binding protein (IGFBP) 4 proteolysis by pregnancy-associated plasma protein-A (PAPP-A) in cells treated with phorbol ester," 379 *Biochem.J.* 57-64 (2004).
Laurence A. Cole, et al., "The Heterogeneity of Human Chorionic Gonadotropin (hCG). III. The Occurrence and Biological and Immunological Activities of Nicked hCG," 129 *BNS* 1559-1567 (1991).
Qiu-Ping Qin, et al., "Double-monoclonal immunofluorometric assays for pregnancy-associated plasma protein A/proeosinophil major basic protein (PAPP-A/proMBP) complex in first-trimester maternal serum screening for Down syndrome," 43 *Clinical Chemistry* 2323-2332 (1997).
Michael T. Overgaard, et al., "Expression of Recombinant Human Pregnancy-associated Plasma Protein-A and Identification of the Proform of Eosinophil Major Basic Protein as Its Physiological Inhibitor," 275 *The Journal of Biological Chemistry* 31128-31133 (2000).
Michael T. Overgaard, et al., "Complex of Pregnancy-associated Plasma Protein-A and the Proform of Eosinophil Major Basic Protein," 278 *The Journal of Biological Chemistry* 2106-2117 (2003).
Oxvig et al., 1201 *Biochimica et Biophysica Acta* 415-423 (1994).
Wu et al., 58 *The Prostate* 345-353 (2004).
Borgono et al, 2 *Mol Cancer Res* 257-280 (2004).
Christiansen et al., 46 *Clin. Chemistry* 1099-1105 (2000).
Chua et al., 275 *J.Biol.Chemistry* 5131-5135 (2000).

(Continued)

*Primary Examiner*—Mark L Shibuya
*Assistant Examiner*—James L Grun
(74) *Attorney, Agent, or Firm*—James C. Lydon

(57) ABSTRACT

A bioaffinity assay for quantitative determination in a sample of free PAPP-A, defined as the pregnancy associated plasma protein A (PAPP-A) that is not complexed to the proform of major basic protein (proMBP), where free PAPP-A is determined either i) as a calculated difference between measured total PAPP-A and measured PAPP-A complexed to proMBP, or ii) by a direct bioaffinity assay measuring only free PAPP-A. Also disclosed is a method for diagnosing an acute coronary syndrome in a person by using as marker either free PAPP-A as such or a ratio free PAPP-A/total PAPP-A, free PAPP-A/PAPP-A complexed to proMBP, or PAPP-A complexed to proMBP/total PAPP-A.

6 Claims, 11 Drawing Sheets

OTHER PUBLICATIONS

Qin, "Maternal Serum Screening for Down Syndrome In the First Trimester With Special Emphasis on Pregnancy Associated Plasma Protein A (PAPP-A)," Ph.D Thesis (Univ. Of Turku, Turku, Finland 1998).

Wittfooth et al., 52 *Clin. Chem.* 1794 (2006).

Oxvig et al., 268 *J. Biol. Chem.* 12243 (1993).

DakoCytomation, "Polyclonal Anti-Human Pregnancy-Associated Plasma Protein A Code No A0230" (Jan. 10, 2005).

Mazerbourg et al., "Pregnancy-Associated Plasma Protein-A (PAPP-A) in Ovine, Bovine, Porcine, and Equine Ovarian Follicles: Involvement in IGF Binding Protein-4 Proteolytic Degradation and mRNA Expression During Follicular Development", 142 *Endocrinology* 5243 (2001).

Lawrence et al., "The Insulin-like Growth Factor (IGF)-dependent IGF Binding Protein-4 Protease Secreted by Human Fibroblasts Is Pregnancy-Associated Plasma Protein-A," 96 *Proc. Nat'l Acad. Sci USA* 3149 (1999).

Durham et al., "Regulation of Insulin-like Growth Factor Binding Protein 4 By A Specific Insulin-like Growth Factor Binding Protein 4 Proteinase In Normal Human Osteoblast-like Cells: Implications in Bone Cell Physiology," 9 *J. Bone Min.I Res.* 111 (1994).

"(ELISA)," Http://en.wikipedia.org/wiki/ELISA.

51 *Clin. Chem.* Table of Contents (Jan. 2005).

Moos et al., "Follicular Fluid and Serum Levels of Inhibin A and Pregnancy-Associated Plasma Protein A In Patients Undergoing IVF," 91 Fertility and Sterility 1739 (2008).

Midgley, "Direct and Indirect Free Thyroxine Assay Methods: Theory and Practice," 47 *Clin. Chem.* 1353 (2001).

* cited by examiner

METHOD FOR DIAGNOSING ACUTE CORONARY SYNDROME

This application is a U.S. National Stage of International Application PCT/FI2005/000036, filed Jan. 19, 2005, which claims benefit of U.S. Provisional Application Ser. No. 60/539,431, filed Jan. 28, 2004.

FIELD OF THE INVENTION

This invention relates to a bioaffinity assay for quantitative determination in a sample of free PAPP-A, defined as the pregnancy associated plasma protein A (PAPP-A) that is not complexed to the proform of major basic protein (proMBP). The invention relates further to a method for diagnosing acute coronary syndrome in a person by using free PAPP-A as a marker.

BACKGROUND OF THE INVENTION

The publications and other materials used herein to illuminate the background of the invention, and in particular, cases to provide additional details respecting the practice, are incorporated by reference.

Pregnancy-associated plasma protein A (PAPP-A) was first identified in the early 1970s as a high-molecular weight constituent found in human late pregnancy serum (1). The concentration in serum increases with pregnancy until term (2). PAPP-A was initially characterized as a homotetramer (1, 3), but it was later demonstrated that circulating PAPP-A in pregnancy was a disulfide-bound 500-kDa heterotetrameric 2:2 complex with the proform of eosinophil major basic protein (proMBP), denoted as PAPP-A/proMBP (4). However, pregnancy serum or plasma is also reported to contain traces (<1%) of uncomplexed PAPP-A (5).

PAPP-A and proMBP are both produced in the placenta during pregnancy but mainly in different cell types. By in situ hybridization, it has been revealed that the vast majority of PAPP-A is synthesized in the syncytiotrophoblast, and all proMBP is synthesized in extravilious cytotrophoblasts (6). Analyses from cloned cDNA demonstrate that the PAPP-A subunit is a 1547-residue polypeptide (7). It contains an elongated zinc-binding motif, three Lin-notch repeats and five short consensus repeats (8).

ProMBP is a glycosylated proteoglycan composed of a strongly acidic 90-residue propiece and a highly basic 117-residue mature form of MBP (9,10). The latter is a cytotoxic protein present in granules of the eosinophil leukoucyte (11). It is released from the eosinophil leukocyte by degranulation, and plays multiple roles in the effector functions of these cells (12). Although in eosinophils mature MBP is generated by proteolytic processing of proMBP, no evidence indicates that MBP can be generated from proMBP of the PAPP-A/proMBP complex. In terms of the role of proMBP in the PAPP-A/proMBP complex, there are studies showing that proMBP acts in vitro as a proteinase inhibitor of PAPP-A (5,13). In addition to PAPP-A, proMBP also forms covalent complex with either angiotensinogen or complement C3dg (14). But the function of proMBP in other complexes remains unknown.

Recently, PAPP-A has been found to be a protease specific for insulin-like growth factors (IGF) binding protein (IGFBP)-4 as well as for IGFBP-5 in vitro (15,16). Notably, the cleavage of IGFBP-4 is in an IGF-dependent manner, whereas the cleavage of IGFBP-5 in an IGF-independent manner. However, the physiological function of PAPP-A in vivo remains to be identified. Insulin-like growth factors-I and -II (IGF-I and IGF-II) play an important role in promoting cell differentiation and proliferation in a variety of biological systems, mediated mainly through the type 1 IGF receptor. The biological activities of IGF-I and -II are modulated by six homologous high-affinity IGF binding proteins, which bind the IGFs and block them from binding to the receptor (17). Cleavage of IGFBP-4 and -5 by PAPP-A causes release of bound IGF, thereby increasing bioavailable IGF for interactions with IGF membrane receptors.

Clinically, reduced serum levels of PAPP-A are associated with Down's syndrome (DS) pregnancies (18). As a marker, PAPP-A is now commonly used for screening for DS in the first trimester (19). Only recently, it has been shown that PAPP-A is present in unstable atherosclerotic (coronary and carotid) plaques (20,21), and that its circulating levels are elevated in patients with acute coronary syndromes (ACS) (20,22). Furthermore, occurrence of PAPP-A in the circulation is an independent prognostic stratifier in patients with coronary artery disease (23). So far little is known about the role of PAPP-A in the plaques. Nonetheless, it has been suggested that increased bioavailability of IGFs through IGFBP-4 proteolysis observed in ACS plays a crucial role in the progression of both coronary atherosclerosis and restenosis (20,24).

Technically, measurability of PAPP-A in the circulation is closely associated with PAPP-A molecule structure. Whether the molecular structure of PAPP-A found in the blood of pregnant women is the same as that found in the blood of ACS patient is particularly important. Until now there is no report dealing with this critical issue. And all the assays used to date for PAPP-A measurement in both situations are based on the antibodies specific for PAPP-A subunit of PAPP-A/proMBP complex (20,25,26,27). From a methodological point of view, this fact makes the circulating PAPP-A in pregnancy indistinguishable from that in ACS.

Here we, for the first time, provide data showing that circulating PAPP-A molecule in pregnancy is different from that in ACS. These findings have important clinical implications for earlier and more specific detection of atherosclerosis related-PAPP-A in the circulation.

OBJECT AND SUMMARY OF THE INVENTION

The object of this invention is to provide a more sensitive and specific method for diagnosing individuals at risk of acute coronary syndrome at an early stage. Particularly, the aim is to achieve a diagnosing method superior to the commonly used assay based on cardiac troponin I and to the proposed assay based on the use of total PAPP-A as a marker.

Thus, according to one aspect, this invention concerns a bioaffinity assay for quantitative determination in a sample of free PAPP-A, defined as the pregnancy associated plasma protein A (PAPP-A) that is not complexed to the proform of major basic protein (proMBP). According to the invention, free PAPP-A is determined either i) as a calculated difference between measured total PAPP-A and measured PAPP-A complexed to proMBP, or ii) by a direct bioaffinity assay measuring only free PAPP-A.

According to another aspect, the invention concerns a method for diagnosing an acute coronary syndrome in a person by using as marker either free PAPP-A as such or a ratio free PAPP-A/total PAPP-A, free PAPP-A/PAPP-A complexed to proMBP, or PAPP-A complexed to proMBP/total PAPP-A.

According to a third aspect, the invention concerns a binder which binds the free PAPP-A but not the PAPP-A complexed to proMBP.

DETAILED DESCRIPTION OF THE INVENTION

Figure 1:
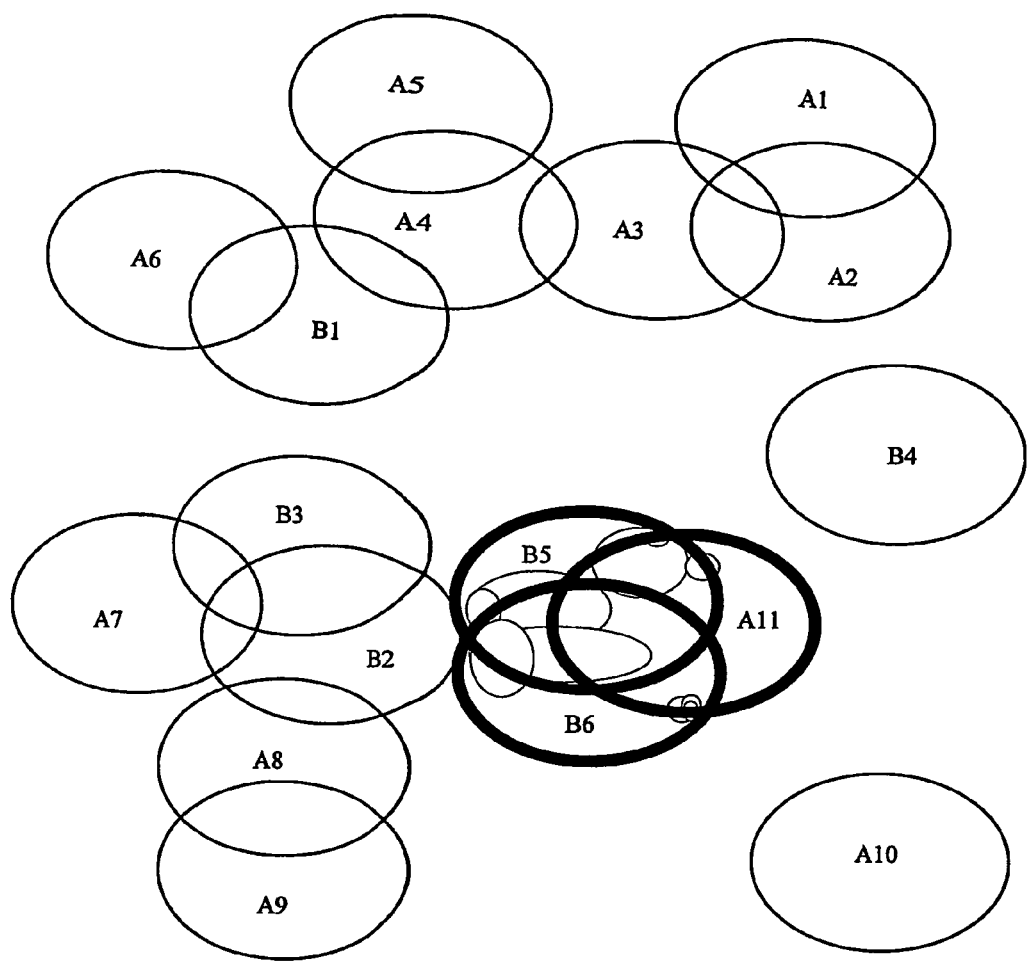
FIG. 1 shows a schematic epitope map of the PAPP-A/proMBP complex. Overlapping circles indicate no possible sandwich formation. Touching circles indicate interfering sandwich formation. Separate circles indicate independent epitopes. Mabs defining epitopes accessible only on proMBP are marked with thick circles, while mabs defining epitopes accessible on PAPP-A are marked with thin circles.

The term "free PAPP-A" shall be interpreted to include any PAPP-A that is not complexed to the proform of major basic protein (proMBP). Thus, "free PAPP-A" will include absolutely free PAPP-A as well as PAPP-A bound to any substance except for proMBP.

The term "binder" shall be interpreted to especially include antibodies and their fragments (optionally genetically engineered), aptamers and protein scaffold derived binders, such as affibodies or fluorobodies. However, the term "binder" is not restricted to the aforementioned examples. Any binder useful in a bioaffinity assay shall be understood to be covered by the definition.

According to one preferable embodiment, free PAPP-A is determined as a calculated difference between measured total PAPP-A and measured PAPP-A complexed to proMBP.

This alternative can, for example, be performed by use of two separate assays, where one aliquot of the sample is exposed to a binder which binds total PAPP-A and the binder is detected to give total PAPP-A. Another aliquot of the sample is exposed to a binder which binds only PAPP-A complexed to proMBP. The binder is detected to give PAPP-A complexed to proMBP. Finally, the amount of free PAPP-A is calculated as a difference between determined total PAPP-A and PAPP-A complexed to proMBP. The two assays can be competitive assays, or more preferably non-competitive sandwich assays, where the specific binders are either capture binders or detecting (labelled) binders.

Alternatively, free PAPP-A and PAPP-A complexed to proMBP can be measured in one single dual analyte assay. The sample can be exposed to a capture binder, which binds total PAPP-A, and to two detecting binders labelled with different labels, so that the first detecting binder labelled with the first label is directed to an epitope present in any PAPP-A molecule, where the signal of the first label is used to give total PAPP-A. The second detecting binder labelled with a second label is directed to an epitope in the proMBP subunit of the molecule, where the signal of the second label is used to give exclusively PAPP-A complexed to proMBP.

The wording "epitope in the proMBP subunit of the molecule" shall be understood to cover epitopes solely within said proMBP subunit as well as epitopes which are partly located in the proMBP subunit and partly in another part of the PAPP-A molecule. Thus, PAPP-A complexed to proMBP can also be measured specifically by binders that only react with epitopes which are partly located in the proMBP subunit and partly in another part of the PAPP-A molecule.

According to another preferable embodiment, free PAPP-A is determined by a direct bioaffinity assay measuring only free PAPP-A. This can, according to one alternative, be performed by exposing the sample to an antibody (including antibody fragments such as Fab and single chain variable (scFv) fragment) or other binder which binds the free PAPP-A but not the PAPP-A complexed to proMBP and detecting the antibody or other binder to give free PAPP-A. Such an antibody or other binder could, for example, be raised to an epitope of PAPP-A which is available only in the molecules not bound to proMBP, such as in the region of amino acids from 381 to 652. A polyclonal antibody specific for free PAPP-A can be raised by immunizing a host animal such as rabbit and sheep with free PAPP-A and an immune adjuvant. While a monoclonal antibody specific for free PAPP-A can be obtained by using hybridoma technology and the same immunogen (here the host animal for immunization is usually mouse). Additionally, an antibody or its fragments such as Fab and single-chain variable fragment (scFv) specific for free PAPP-A can be generated using phage display from either a synthetic or a naïve antibody library. Free PAPP-A can be made available from ACS plaques or from pregnancy PAPP-A that is free of proMBP or from recombinant expression of PAPP-A encoding DNA sequence.

Alternatively, the bioaffinity assay measuring only free PAPP-A could be carried out by making PAPP-A complexed to proMBP non-capable of participating in the bioaffinity reaction in which the sample is exposed to an antibody or other binder binding total PAPP-A. There are two approaches towards achieving this goal. One relates to the use of adsorption as already demonstrated in FIG. 8B, PAPP-A complexed to proMBP was removed in a preceding step by adsorption with mabA11, which then allowed measurement of free PAPP-A. The other relates to the use of blocking strategy in which access for certain PAPP-A subunit-specific antibody or other binder to its epitope is blocked due to the binding of a proMBP reactive antibody/other binder either derivatized with a special group or not. Blocking can take place in a preceding step or simultaneously with the assay. In this way, free PAPP-A can be effectively measured as well.

The invention will be illuminated by the following non-restrictive Experimental Section.

EXPERIMENTAL SECTION

Materials and Methods

Reagents

ITC-TEKES $Eu^{3+}$ fluorescent chelate of 4-[2-(4-isothiocyanatophenyl)ethynyl]-2,6,-bis{[N,N-bis(carboxymethyl)-amino]methyl}pyridine and biotin isothiocyanate (BITC) were obtained from Innotrac Diagnostics Oy. DELFIA assay buffer and wash solution were prepared as described previously (28). Assay buffer supplemented with 0.01% denatured mouse IgG and 0.02% native mouse IgG was referred to as modified assay buffer. Low-fluorescence 12-well Maxisorp microtitration strips (ultraviolet-quenched) were purchased from NUNC. Streptavidin-coated single wells and strips were obtained from Innotrac Diagnostics Oy. Bovine serum albumin (BSA) was purchased from Intergen. NAP-5™ and NAP-10™ columns were from Pharmacia Biotech. All other chemicals used were of analytical grade.

Six monoclonal antibodies denoted as mabB1, 2, 3, 4, 5, and 6, specific for the PAPP-A/proMBP complex, were gifts of Dr. Michael Christiansen from State Serum Institute, Denmark. Other eleven monoclonal antibodies denoted as mabA1, 2, 3, 4, 5, 6, 7, 8, 9, 10, and 11, also specific for the PAPP-A/proMBP complex, were gifts of Dr. Maria Severina from HyTest Oy, Finland Calibrators were prepared by diluting a filtrated (through a 0.22 µm pore size filter) pool of ten $3^{rd}$-trimester pregnancy sera in a buffer containing 60 g/L bovine serum albumin, 50 mmol/L Tris-HCl (pH 7.75), 15 mmol/L NaCl, and 0.5 g/L NaN3, and calibrated against the third-trimester pregnancy pooled serum-derived WHO IRP 78/610 for pregnancy-associated proteins (WHO International Laboratory for Biological Standards, Statens Serum Institut, Copenhagen, Denmark). Levels of PAPP-A and proMBP were expressed in milliunits per liter. The calibrators were stored at −20° C. until use.

Serum Samples

Eight patients (4 males aged 57±5 years and 4 females aged 81±3 years) with ACS had prolonged chest pain accompanied by ST-segment elevation and abnormally increased levels of CKMB and cTn I. From these patients, serum samples were taken on admission to the Department of Cardiology, Turku University Central Hospital and at 1, 2, 4, 6, 24, 48 and 72 hours afterward. In addition, 2 first-trimester serum samples (gestational age: weeks 9 and 11) were included in this study. All the serum samples were obtained with informed consent. The procedures followed were in accordance with the Helsinki Declaration of 1975 as revised in 1996. All samples were stored at −20° C. (pregnancy samples) or −70° C. (ACS samples) before the measurement.

Labeling of Antibodies with Lanthanide Chelate and Biotin

Intrinsically fluorescent europium chelate was used for labeling of the antibodies (29). Labeling reactions were performed as reported previously (25). Briefly, antibody was labeled overnight (16-20 h) at room temperature with a 100-fold molar excess of chelate in 50 mmol/L sodium carbonate buffer (pH 9.6). The labeled antibodies were separated from excess free chelate and aggregated proteins on a Superdex 200 HR 10/30 gel filtration column (Pharmacia Biotech, Sweden) operated with 50 mmol/L Tris-HCl (pH 7.75), 15 mmol/L NaCl, 0.5 g/L NaN3 at 25 mL/h. Fractions of 0.45 mL were collected. The fractions containing labeled antibody were pooled, and the degree of labeling was determined with a europium calibration solution. The labeling degrees of the antibodies were between 5 and 15 of $Eu^{3+}$ chelates per molecule of IgG.

Biotinylation of antibodies was conducted with a 50-fold molar excess of biotin-isothiocyanate in 50 mmol/L sodium carbonate buffer (pH 9.6) at room temperature for 3 h. The biotinylated antibody was separated from free biotinylation reagent by passing the reaction mixture through NAP-5™ and NAP-10™ columns (Amersham Biosciences AB) with 50 mmol/L Tris-HCl (pH 7.75), 15 mmol/L NaCl, 0.5 g/L NaN3 as eluent. BSA was added to a final concentration of 1 g/L, and the solution was filtered through a 0.22 µm pore size filter and stored at 4° C.

Epitope Mapping

All antibodies against the PAPP-A/proMBP complex were tested in pairs with each used as a capture or a detection antibody. A one-step sandwich assay format was used together with a 100 mIU/L PAPP-A calibrator and a blank solution. The procedure used was similar to that described earlier (30). Briefly, 10 µL of PAPP-A calibrator or blank solution and 100 ng of $Eu^{3+}$-labeled antibody in 20 µL of assay buffer were added, in triplicate, to wells directly coated with 0.4 µg of antibody. Subsequent incubation was performed at 37° C. for 10 min and 60 min with shaking (900 rpm, iEMS Incubator/Shaker, Labsystems Oy, Finland). After that, the wells were washed six times and dried with a stream of hot dry air for 5 min; the fluorescence was then measured with a Victor™ 1420 multilabel counter (Perkin-Elmer Life Sciences, Wallac Oy, Finland).

Immunoassays

Two immunoassays were used in this study. One denoted as assay T, configured with the biotinylated mabA1 and europium labeled mabB4; and the other denoted as assay C, configured with the biotinylated mabA1 and europium labeled mabA11, were performed in a conventional microplate assay format with the iEMS Incubator/Shaker. For both assays, first, the biotinylated mabA1 was immobilized on to the surface of streptavidin-coated microtiter wells by incubating 300 ng of biotinylated mab A1 in 50 μL of DELFIA assay buffer per well for 60 min at RT with slow shaking. Unbound biotinylated antibody was removed by washing the wells. Then, for the assay T, 10 μL of calibrator or sample and 200 ng of the $Eu^{3+}$-labeled mabB4 in 20 μl of modified assay buffer were added per well. The wells were incubated for 30 min at 37° C. with slow shaking and washed 6 times. After that, the wells were dried for 5 min and the time-resolved europium fluorescence was measured directly from the dry surface with the Victor™ 1420 multilabel counter. The concentrations of unknown samples were obtained by calibrating their fluorescence signals against a calibration curve derived from the calibrator wells by the MultiCalc immunoassay program (Perkin-Elmer Life Sciences, Wallac Oy, Finland) with the use of a spline algorithm on logarithmically transformed data. For the assay C, 10 μL of calibrator or sample and 20 μl of the modified assay buffer were added to each well. The wells were incubated for 30 min at 37° C. with slow shaking, and washed twice. After that, 300 ng of the $Eu^{3+}$-labeled mabA11 in 30 μL of the modified assay buffer was added per well, and the wells were incubated for 30 min at 37° C. with slow shaking, and washed 6 times. The following steps were the same as for the assay T.

Gel Filtration Chromatography

This was carried out on a Superose™ 6 (3.2×300 mm) precision column PC3.2/30 (Pharmacia Biotechnology, Sweden) equilibrated and eluted with 50 mmol/L sodium phosphate buffer, pH 7.0, containing 0.15 mol/L NaCl, and 0.02% $NaN_3$ at the flow rate of 0.04 mL/min. Fifty μl of sample (serum diluted twofold in elution buffer and filtered through 0.22 μm pore-size filter) was loaded. The column effluent was monitored at 280 nm, and after 0.6 ml of initial elution, 100 μL fractions were collected. The total run time was 75 min. The column was operated at 10° C. on a Pharmacia SMART system (Pharmacia Biotechnology, Sweden) and calibrated with the following proteins: Thyroglobulin (669 kDa), Apoferritin (481 kDa), Immunoglobulin G (160 kDa), Bovine serum albumin (67 kDa), Chymotrypsinogen A (25 kDa) and Ribonuclease A (13.7 Kda). Both first-trimester pregnancy serum specimens and ACS serum samples were fractionated by the gel filtration chromatography.

Adsorption of PAPP-A from Normal Serum Samples

This was performed with the use of streptavidin-coated microtitration wells and biotinylated mabA1 or biotinylated A11. Thirty μl of serum sample was added to each well in which 300 ng of bioA1 or 400 ng of bio-mabA11 was already immobilized on the surface. For bioA1, incubation was carried out at RT for 1 h with slow shaking. After that, 10 μl of treated serum taken from each well was applied to above immunoassays for PAPP-A measurement. For bioA11, incubation was carried out at RT for 1 h with slow shaking, the serum sample was then transferred to another coated well and followed with 1 h incubation. After that, transfer step and incubation was repeated until third incubation was conducted.

Finally, 10 μl of treated serum was applied to above immunoassays for PAPP-A measurement.

Statistical Analysis

Statistical analysis was conducted using StatView (SAS Institute, Cary, USA).

Results

Epitope Map of Pregnancy PAPP-A Defined by 17 Mabs

A schematic epitope map shown in FIG. 1 was constructed according to data obtained from every possible two-site combination of the antibodies. Relationships of the location of each antibody were determined on the basis of whether the binding of one antibody would allow or interfere with independent binding of another antibody. Of the 17 mabs, B1, 2, 3, and 4 were previously shown to be specific for binding to PAPP-A subunit of the PAPP-A/proMBP complex, whereas B5 and B6 were reactive with proMBP subunit of the PAPP-A/proMBP complex (5,31). MabA11 was able to form sandwiches with all the other mabs except for mabB5 and B6, indicating that it should react with proMBP subunit of the PAPP-A/proMBP complex. Of the rest 14 antibodies reactive with PAPP-A subunit of the PAPP-A/proMBP complex, two antibodies (A10 and B4) did not share their epitopes with other antibodies.

Calibration Curves

Figure 2:
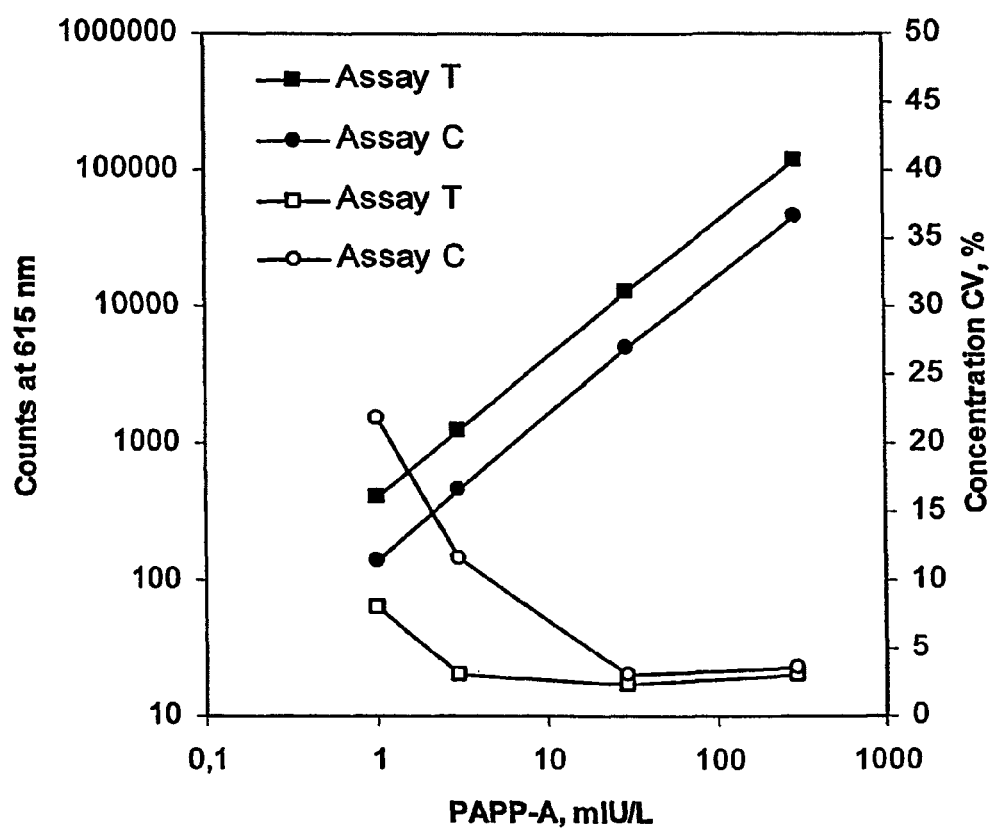
FIG. 2 shows calibration curves and imprecision profiles for assay T (assay T=assay for total PAPP-A) configured with two PAPP-A subunit-specific monoclonal antibodies (A1/B4) and assay C (assay C=assay for PAPP-A complexed to proMBP) made from a proMBP subunit-specific monoclonal antibody for detection and a PAPP-A subunit-specific monoclonal antibody for capture (A1/A11). Four replicates were used for each concentration. Curves with filled characters relate to counts and curves with open characters relate to concentration CV.

The calibration curves of the two assays shown in FIG. 2 were obtained with a standard material derived from a pool of third-trimester pregnancy sera. Both curves were linear over the concentrations ranging from 1.0 mIU/L to 300 mIU/L. For the assay T, assay imprecision was low with intra-assay concentration CVs of below 10 over the range from 1.0 mIU/L to 300 mIU/L. For the assay C, assay imprecision was over 20% at 1.0 mIU/L and below 15 over the range from 3.0 mIU/L to 300 mIU/L. More importantly, both calibration curves were parallel to each other, indicating that PAPP-A in the standard material is equally detected by the two assays.

Molecular Profile and Immunoreactivity of Pregnancy PAPP-A

Figure 3:
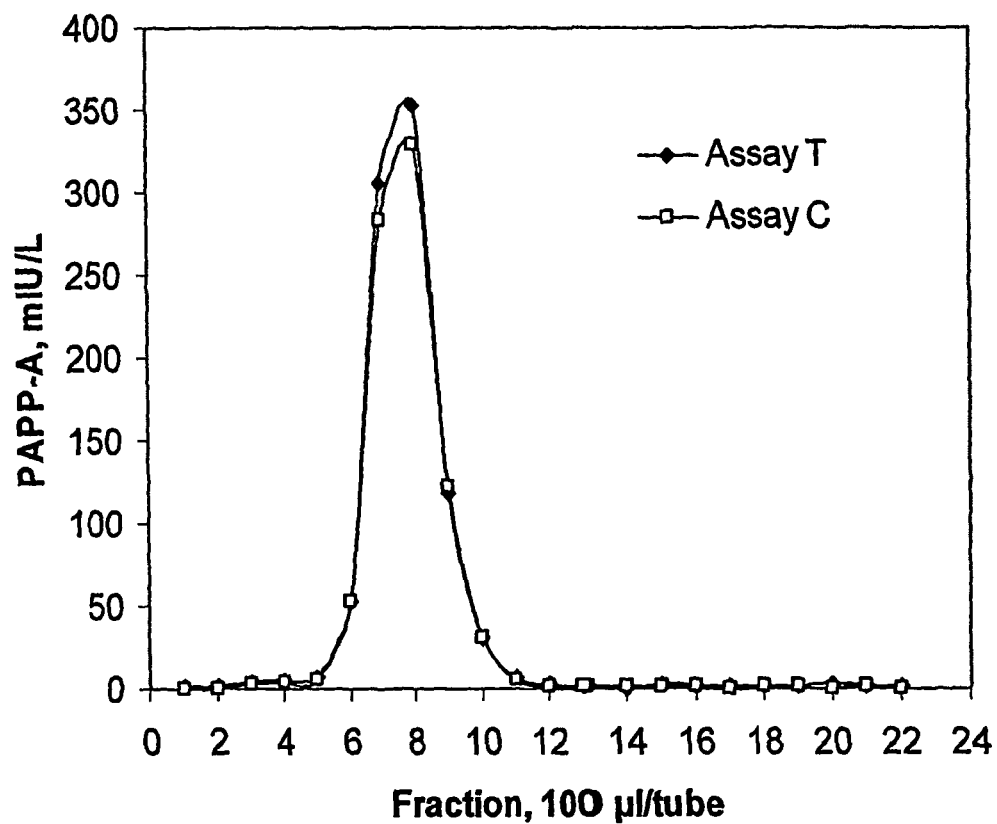
FIG. 3 shows gel filtration of a first-trimester serum sample on a Superose™ 6 precision column (PC3.2/30). PAPP-A was detected by assay T, and by assay C. The PAPP-A/proMBP eluted as a single peak at the position where thyroglobulin (669 kDa) was eluted.

A first-trimester serum sample was fractionated by size-exclusion chromatography and the fractions were analyzed by the two immunoassays. Pregnancy PAPP-A revealed by the two assays as a single peak eluted at the same position in which thyroglobulin (669 kDa) was eluted (shown in FIG. 3). Furthermore, the two peaks obtained by the two assays totally overlapped with each other.

The PAPP-A concentrations measured by the assay T were slightly higher than those measured by the assay C.

PAPP-A in ACS Patients

Figure 4:
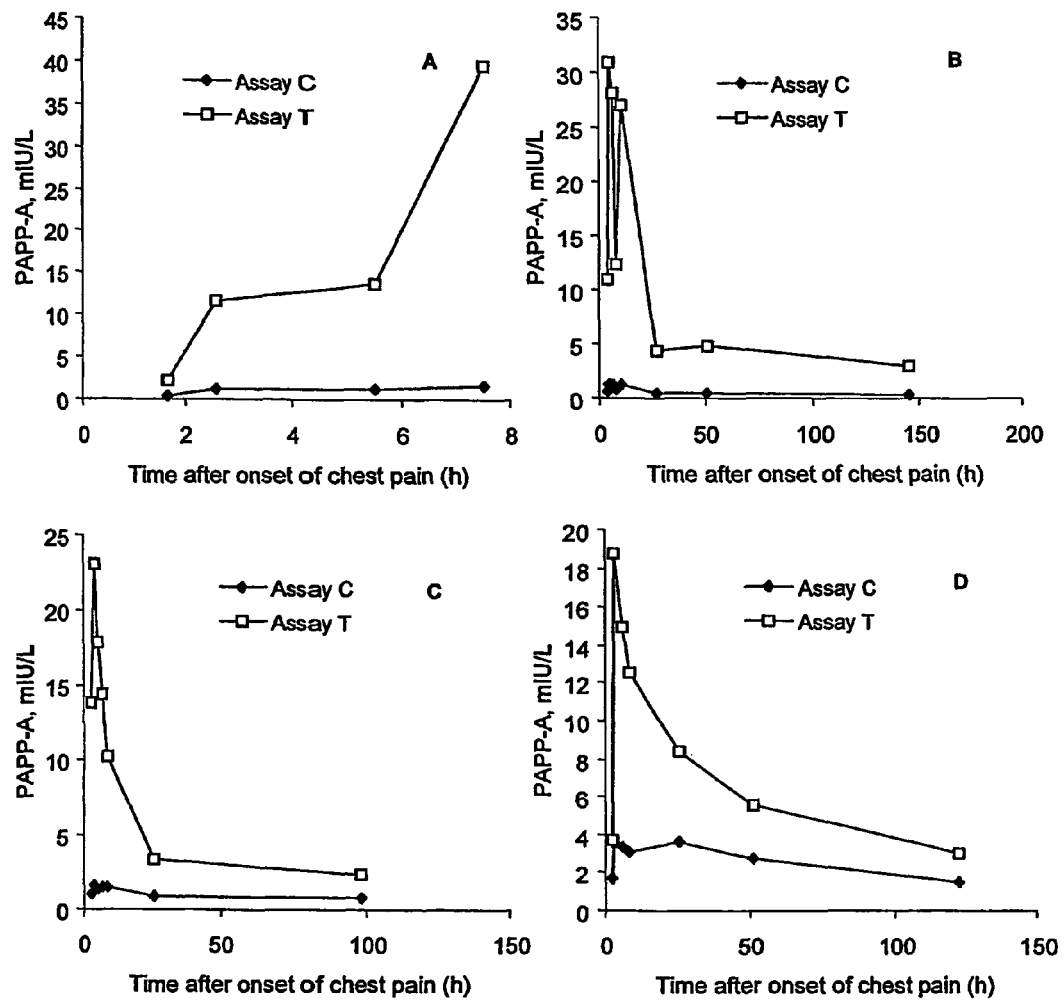
FIG. 4 shows serum kinetics of PAPP-A for patients with ACS. PAPP-A was detected by the assay T, and by the assay C.

PAPP-A levels in serial serum samples from 4 patients with ACS were measured by the two assays. Using the assay T, PAPP-A levels above the reference level of 5.68 mIU/L (22) were observed in all 4 patients at different times after the onset of chest pain (shown in FIG. 4). Although the degree of maximal increase in PAPP-A levels was varied, a marked increase in PAPP-A levels appeared in all the 4 ACS patients early within 2 h after the onset of chest pain. Using the assay C, no significant increase in the levels of PAPP-A was found in these 4 patients, in which the concentrations of PAPP-A were below 4 mIU/L for all serum samples. The results show that ACS specific PAPP-A present in the circulation is undetectable by the proMBP-reactive antibody.

Molecular Profile and Immunoreactivity of ACS PAPP-A

Figure 5:
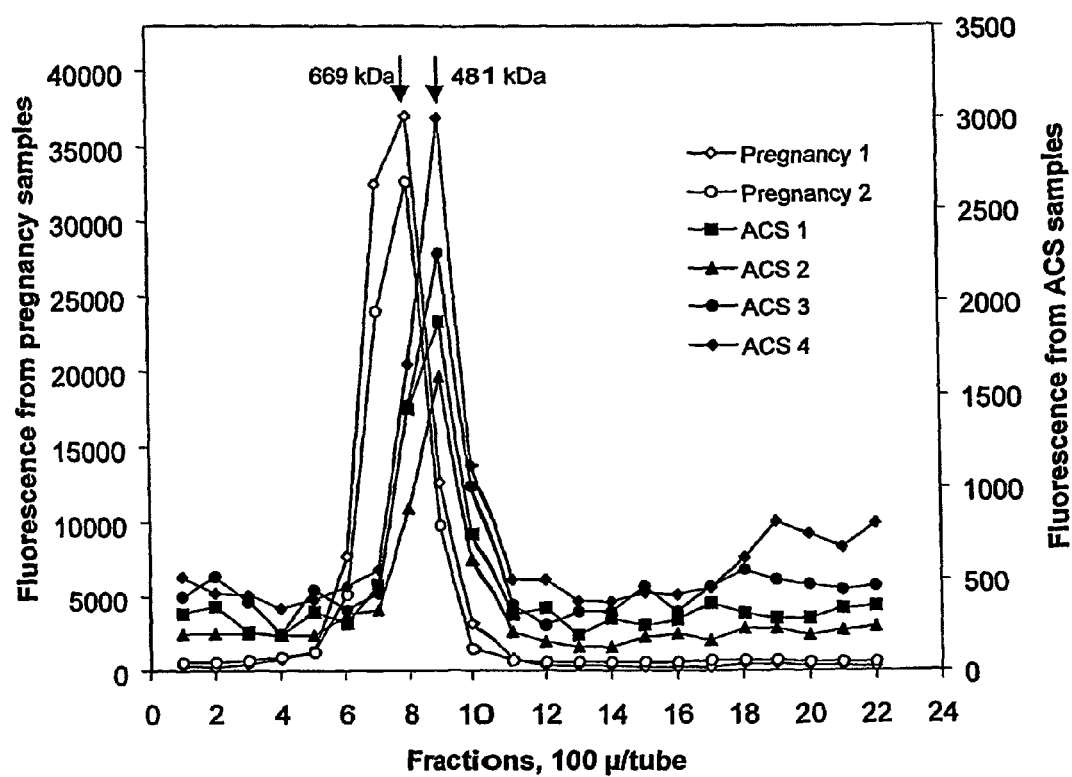
FIG. 5 shows comparison by gel filtration of 4 ACS serum samples with two first-trimester serum samples on a Superose™ 6 precision column (PC3.2/30). PAPP-A was detected by the assay T. The ACS PAPP-A eluted as a single peak at the position where apoferritin (481 kDa) was eluted.
Figure 6:
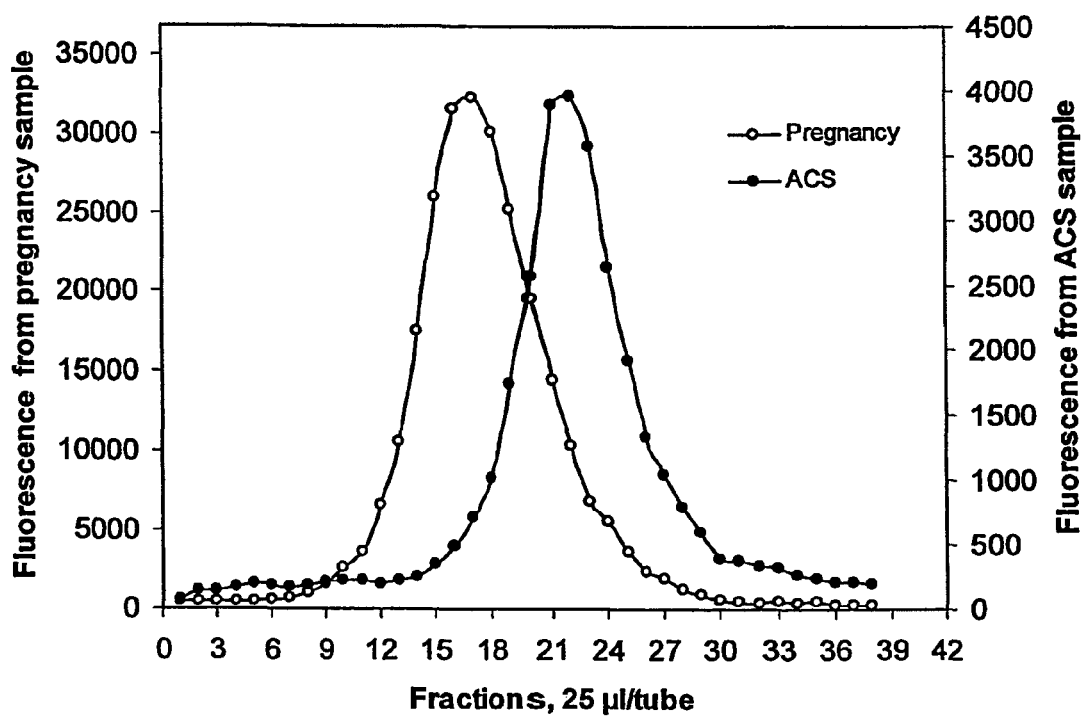
FIG. 6 shows comparison by gel filtration of 1 ACS serum sample (solid characters) with 1 first-trimester serum sample (open charactes) on a Superose™ 6 precision column (PC3.2/30). PAPP-A was detected by the assay T.

Four serum samples with markedly increased level of PAPP-A obtained from another 4 patients with ACS were fractionated by size-exclusion chromatography. Fractions were analyzed by the assay T. A single peak of PAPP-A immunoreactivity eluted at a position in which apoferritin (481 kDa) was found (shown in FIG. 5). Elution patterns from all 4 ACS serum samples were the same regardless of the concentrations of PAPP-A, and clearly shifted from the two pregnancy samples (669 kDa). The difference in molecular size between the pregnancy PAPP-A and ACS PAPP-A was clearly demonstrated in FIG. 5, and became much more pronounced in FIG. 6 when fractionation was conducted with a smaller fraction volume (25 μl).

PAPP-A in Normal Subjects

Serum PAPP-A levels in normal subjects (n=130, aged between 50 and 69 years) were less than 7.6 mIU/L, with a median value of 3.0 mIU/L. Such levels of circulating PAPP-A found in normal subjects were detectable not only by the assay T but also by the assay C.

Figure 7:
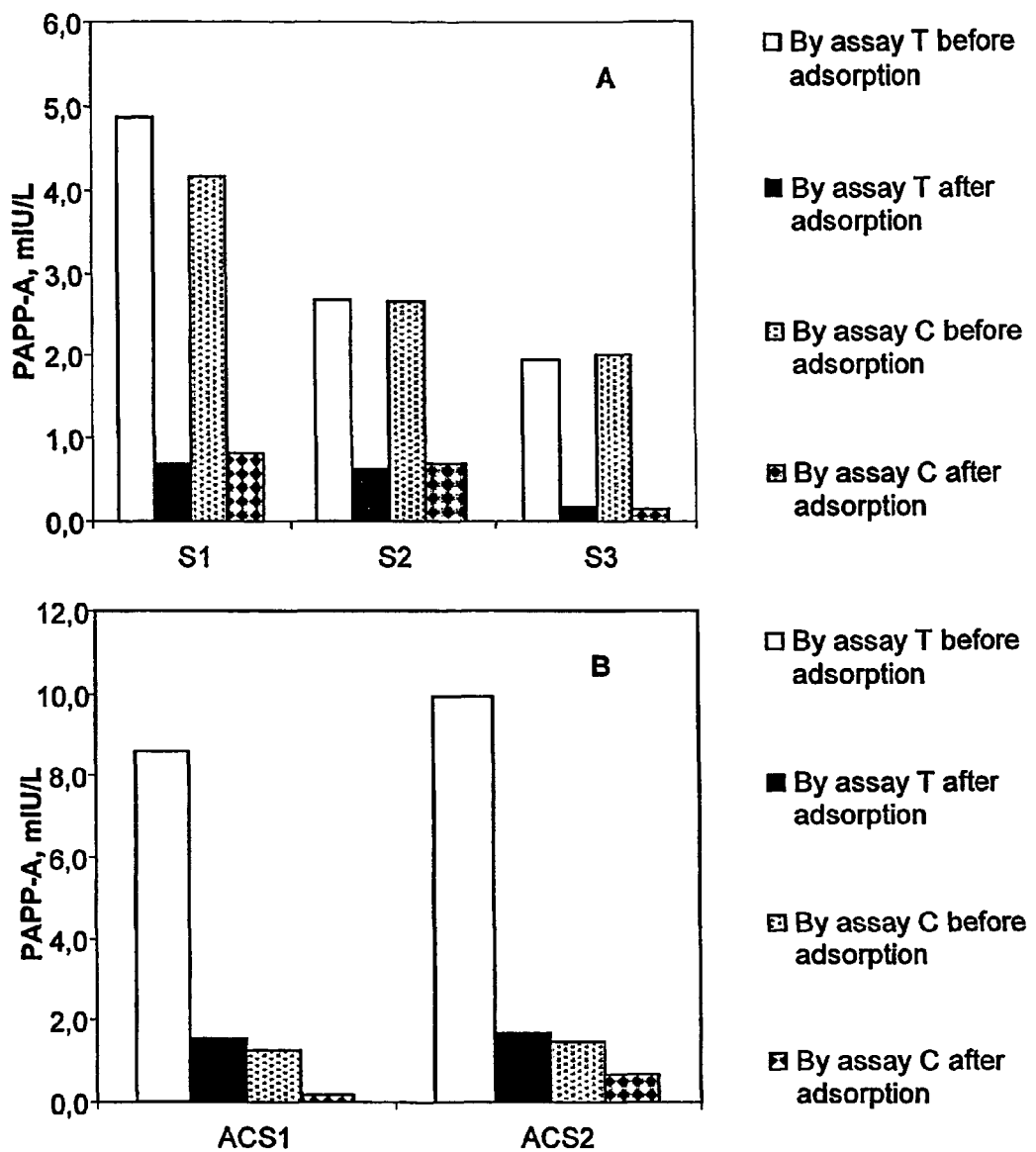
FIG. 7A shows PAPP-A in 3 normal serum samples (denoted as S1, S2 and S3) before and after adsorption treatment with mabA1.
FIG. 7B shows PAPP-A in 2 ACS serum samples (denoted as ACS1 and ACS2) before and after adsorption treatment with mabA1.
Figure 8:
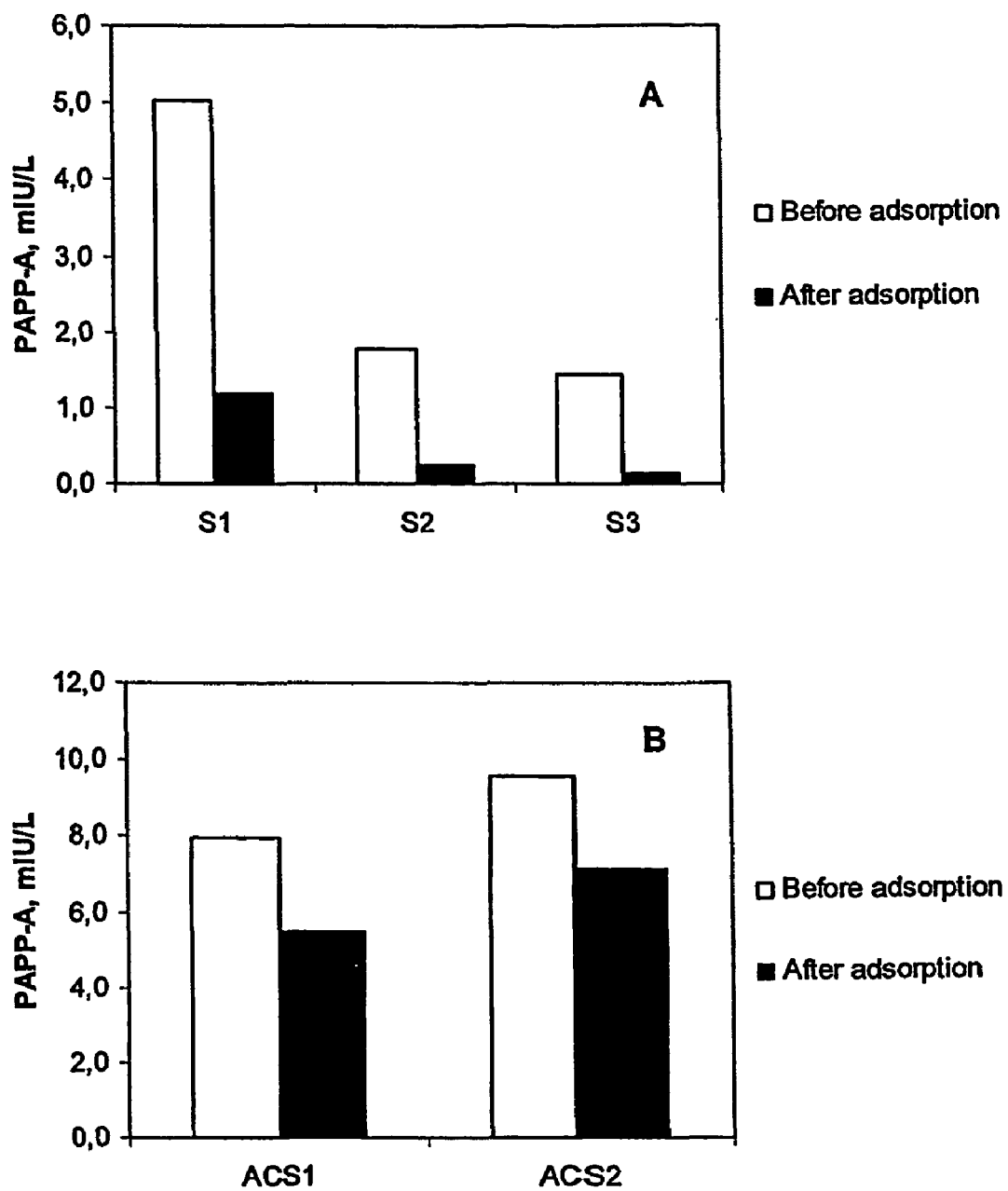
FIG. 8A shows PAPP-A in 3 normal serum samples (denoted as S1, S2 and S3) before and after adsorption treatment with mabA11.
FIG. 8B shows PAPP-A in 2 ACS serum samples (denoted as ACS1 and ACS2) before and after adsorption treatment with mabA11. PAPP-A levels were measured by the assay T.

FIG. 7A shows that low levels of circulating PAPP-A found in normal subjects were detectable by the assay T as well as by the assay C. In addition, adsorption treatment could be used to remove PAPP-A from the normal sera by either PAPP-A subunit-specific antibody A1 (FIG. 7A) or proMBP-specific antibody A11 (FIG. 8A).

PAPP-A in ACS Subjects

PAPP-A in ACS patients can be classified into two categories, i.e., proMBP complexed form and proMBP uncomplexed form, which together form the total PAPP-A detected by the assay T. The proMBP complexed form constitutes the basal level of PAPP-A and can be specifically detected by the assay C. The proMBP uncomplexed form relates to the ACS and can be specifically determined by delta value obtained from use of the both assays mentioned above or dual-label assay or blocking assay or, in particular, free PAPP-A specific assay.

FIG. 7B shows that PAPP-A (both proMBP-complexed and -uncomplexed forms) in ACS patients could be measured by the assay T, whereas the proMBP-complexed form (ACS-irrelevant) could be measured by the assay C. Adsorption with mabA1 effectively removed both the proMBP-complexed and -uncomplexed forms (FIG. 7B), however, adsorption with mabA11 only removed the proMBP-complexed form (FIG. 8B), thereby allowing the uncomplexed form, namely free PAPP-A to be detected.

Figure 9:
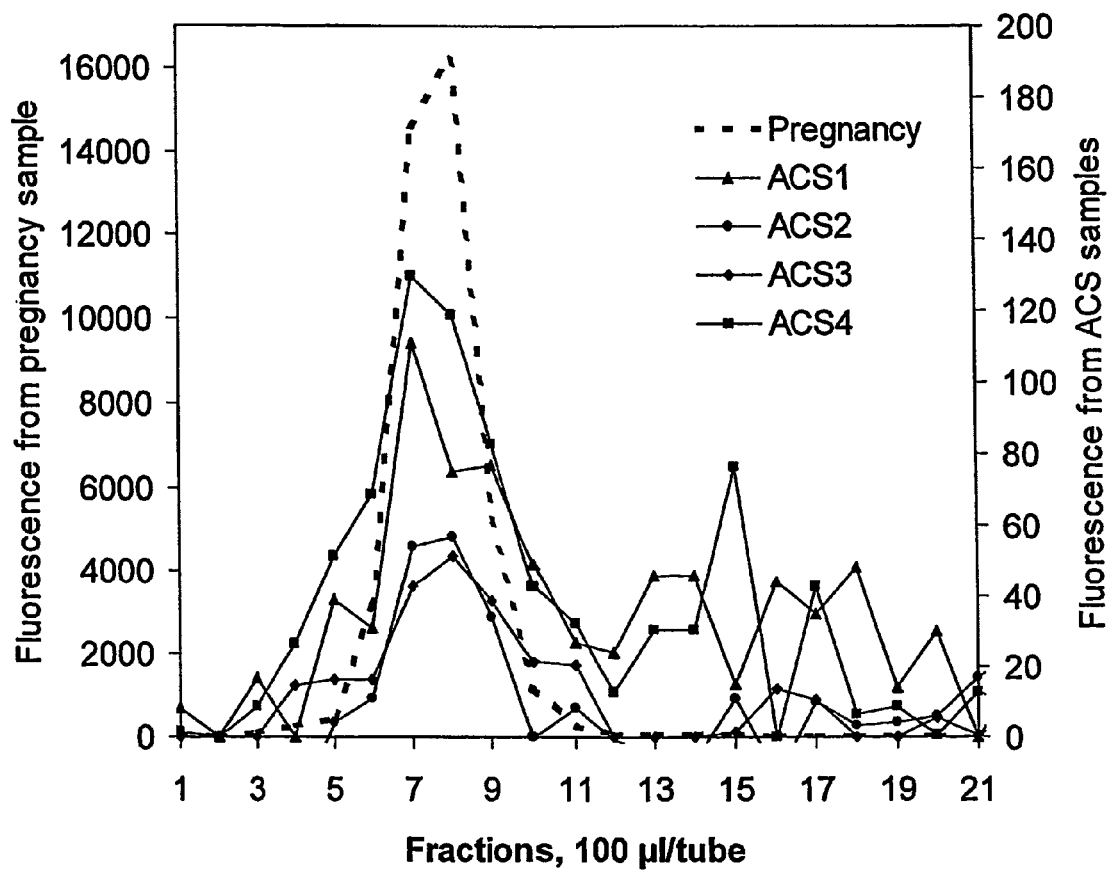
FIG. 9 shows gel filtration of 4 ACS serum samples (denoted as S1S2, S3 and S4) and a first-trimester serum sample on a Superose™ 6 precision column (PC3.2/30). Fractions were analysed using the assay C.

Analysis of fractions from ACS serum samples and from pregnancy serum sample reveals that prominent signals detected by the assay C indeed coincided with that of pregnancy PAPP-A, which is known to be a complex with proMBP (see FIG. 9).

Distribution of Basal PAPP-A Levels in Normal Subjects

Figure 10:
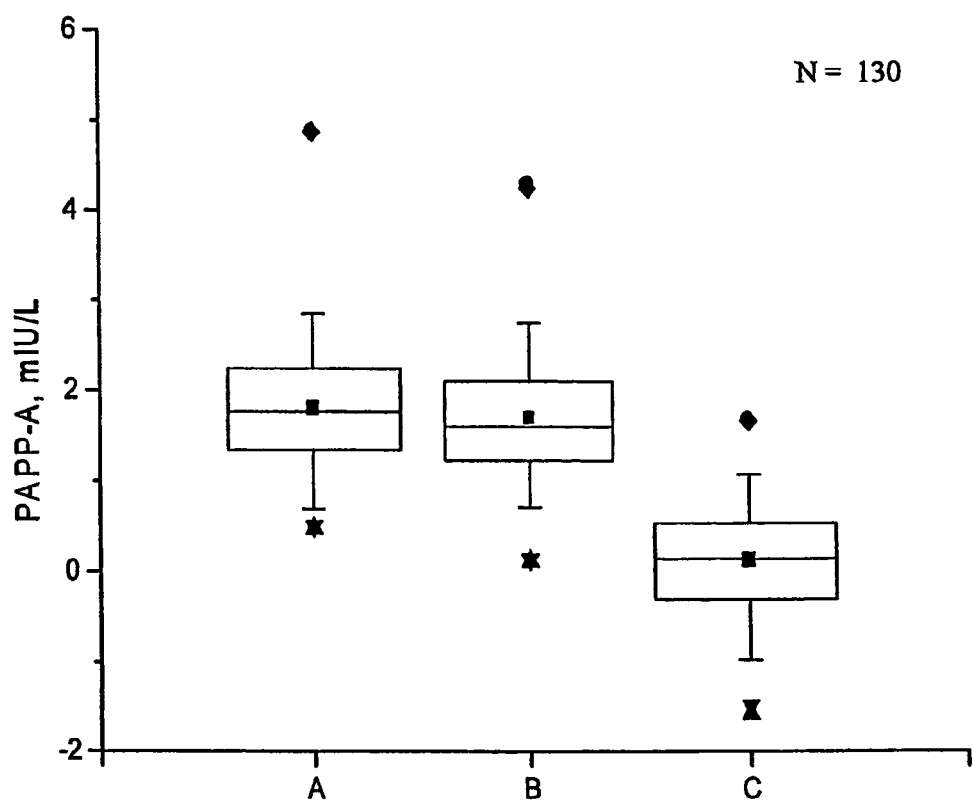
FIG. 10 illustrates box-and-whisker plots showing distributions of PAPP-A concentrations and delta values (defined as the difference between the PAPP-A values obtained by the assay T and the assay C) in normal subjects. Plot 1, PAPP-A concentrations determined by the assay T. Plot 2, PAPP-A concentrations determined by the assay C. Plot 3, Delta values derived from PAPP-A concentrations measured by the two assays. The boxes indicate the 25th-75th percentiles; the whiskers indicating the 5th and 95th percentiles. All values above the 95th percentile and below the 5th percentile are plotted separately as •. The horizontal lines indicate the medians; and the dashed boxes indicate the means.

PAPP-A concentrations determined by the assay C were found to be correlated with those measured by the assay T using only PAPP-A subunit-specific antibodies in 130 normal aged men (Y=0.6131+0.59669X, R=0.63, P<0.001). FIG. 10 shows Box plots of data distribution properties for serum PAPP-A concentrations measured by the two assays, respectively, and for delta values in relation to a normal aging population. Apart from that, histograms indicate that distribution of delta values is least skewed and has a kurtosis value of 0.1 while distributions for PAPP-A concentrations are positively skewed and have much greater kurtosis values (3.47 and 1.58, respectively). Due to the compatibility with the Gaussian distribution, a suitable decision limit for the delta value can be derived.

Clinical Usefulness of the Delta Value

The delta value, in principle, reflects only the ACS-relevant PAPP-A. It is thus not affected by the influence of basal PAPP-A levels. The basal PAPP-A levels are variable from patient to patient, which can be a source of interference with the outcomes of the measurements (false negatives and false positives) made by the assay using only PAPP-A subunit-specific antibodies.

Figure 11:
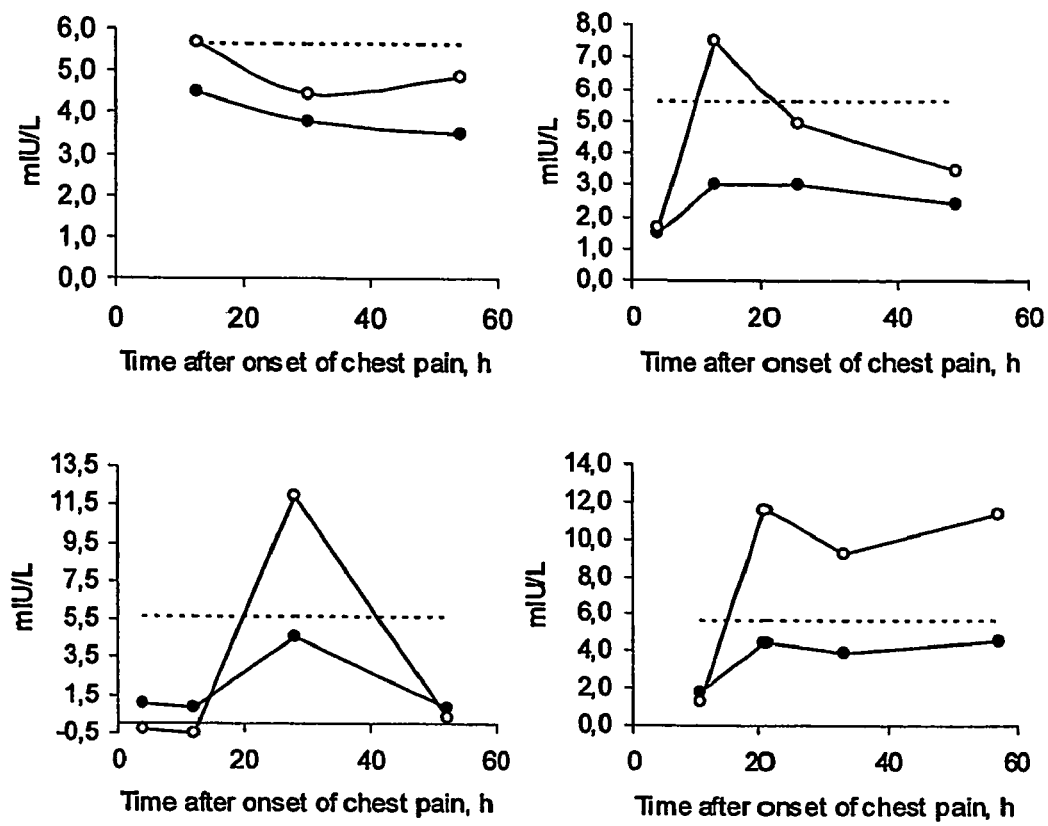
FIG. 11 shows application of delta values (lines with open circles) in ACS patients as compared to the use of total PAPP-A concentrations (lines with solid circles). Delta values and the relevant decision limit are normalized according to the 97.5% upper reference limit for total PAPP-A concentrations. The dotted line indicates the decision limit for both the delta values and total PAPP-A concentrations.

To address the possible false negative problem, we analysed serial serum samples from a subgroup of 29 ACS patients (cTnI was elevated with all these patients) with the two assays. When a decision limit was a 97.5% upper reference limit (5.68 mIU/L) derived from PAPP-A concentrations of normal subjects with the assay using only PAPP-A subunit-specific antibodies, all patients were PAPP-A-negative. However, when a decision limit was based on delta values defined as mean+3 SD, 20 out of 29 patients turned to be PAPP-A-positive. FIG. 11 shows some examples of comparisons between the uses of two decision limits.

Antibody Combinations for Measuring Total PAPP-A, or PAPP-A in Complex with proMBP or Free PAPP-A All possible two-site combinations of antibodies currently available were characterized with pregnancy-derived PAPP-A and ACS-related PAPP-A obtained from atherosclerotic plagues (also called atherosclerosis- or plaque-derived PAPP-A). As shown in Table 1, three kinds of assays or antibody combinations were found. Firstly, antibody combinations for total PAPP-A generated high specific signals for both pregnancy-derived PAPP-A and ACS-related PAPP-A, meaning that these assays are equally suitable for the measurement of pregnancy-derived PAPP-A and ACS-related PAPP-A. Secondly, antibody combinations recognising PAPP-A/proMBP only generated high specific signal with pregnancy-derived PAPP-A but not with ACS-related PAPP-A, indicating that these assays are only suitable for the measurement of pregnancy-related PAPP-A. A third type of antibody combination (such as 3C8/7A6) generated a low specific signal for the pregnancy-derived PAPP-A, but high specific signal for ACS-related PAPP-A which preferentially consists of a free or non-complexed form of PAPP-A. Since the molecular form of PAPP-A in non-pregnant, non-ACS individuals is similar to the form (i.e. PAPP-A/proMBP) found in pregnancy, assays like this are preferably suitable for the specific measurement of the ACS- or atherosclerosis-related PAPP-A.

In summary, basal levels PAPP-A, present as a PAPP-A/proMBP complex, fluctuate frequently from sample to sample. In ACS patients lesion-relevant PAPP-A is only detected by the total assay rather than the complex assay. On the other hand basal level PAPP-A can be detected by the both assays. The fact lays the foundation for the use of free PAPP-A or delta value (which indirectly reflects free PAPP-A) that eliminates the influence from fluctuation of individual changes in the basal levels of PAPP-A. Decision limit built on free PAPP-A or delta value is thus more rational than that simply based on the total PAPP-A concentrations, and allows accurate measurement of ACS PAPP-A in the circulation.

Discussion

We have demonstrated that circulating PAPP-A in pregnancy is different from that in ACS. We first confirm that pregnancy PAPP-A is a complex with proMBP as it can be equally determined using antibodies against either PAPP-A subunit or proMBP subunit as tracer. Second, we show evidence that ACS related PAPP-A is not complexed with proMBP as it can only be determined by antibodies against the PAPP-A subunit. This was also confirmed by assays using two other proMBP reactive antibodies, i.e., mabB5 and B6 (data not shown). Third, our results show that pregnancy related PAPP-A is bigger in molecular size as compared to ACS related PAPP-A, which further unequivocally shows that ACS related PAPP-A differs from pregnancy PAPP-A.

There are two reasons that can make the epitope recognized by the monoclonal antibody A11 undetectable. Firstly, the epitope is lost either by lack of the subunit that bears the epitope or by modification that causes changes in molecular conformation. Secondly, the epitope is blocked from binding of the antibody by either covalent lining the epitope to another macromolecular substance or by an interfering factor that is present only in the ACS serum samples. Because normal recovery results (data not shown) have been obtained by spiking pregnancy PAPP-A into the ACS serum samples, the possibility of presence of the interferant in the ACS samples can be excluded. Moreover, due to the finding that ACS PAPP-A is clearly smaller in molecular size than pregnancy PAPP-A, modification of the PAPP-A/proMBP complex including bridging to a further substance seems very unlikely. It is thus evident that ACS PAPP-A in the circulation is not complexed with proMBP.

On average, ACS PAPP-A present in the circulation is around 20 mIU/L (22,23), which is equivalent to about 6 μg/L (26). Such low concentrations make it difficult to detect ACS PAPP-A directly from blood samples by SDS-polyacrylamide gel electrophoresis (PAGE) and Western blot analyses. Therefore, other detection technologies with high sensitivity and specificity are needed for the relevant investigations. Time-resolved fluorometry of lanthanide chelates is one of the most sensitive detection technologies that currently exist (27). Using this technology and specific antibodies, two immunoassays for total PAPP-A and PAPP-A complex with proMBP were built. As expected, superior sensitivities of these assays allowed detection of total PAPP-A and proMBP-complexed PAPP-A directly from the blood samples.

In pregnancy, over 99% of PAPP-A in the circulation is present as a disulfide-bound 500 kDa 2:2 complex with proMBP, and less than 1% of PAPP-A is present as a dimer (5). In the PAPP-A/proMBP complex, PAPP-A is dimerized by a single disulfide bond, and proMBP is dimerized by two disulfide bonds; each PAPP-A subunit is connected to a proMBP subunit by two disulfide bonds (32). Recent studies show that covalent binding is needed for proMBP inhibition of the catalytic activity of PAPP-A, but detailed mechanism about formation of the complex remains largely unknown.

So far, no free form of proMBP has been found in the circulation, although serum levels of proMBP reportedly exceed those of PAPP-A 4 to 10-fold on a molar basis throughout pregnancy (14). The rest of circulating proMBP in pregnancy is present in two other types of complexes, namely a 2:2 disulfide-bound complex between proMBP and angiotensinogen and a 2:2:2 complex between proMBP, angiotensinogen, and complement C3dg (14). In this study, two-step format was used for the assay involving the use of the proMBP-specific antibody as tracer. The assay with this format effectively prevented other proMBP complexes present in the pregnancy serum from reacting with the europium labelled proMBP-specific antibody, thereby allowing specific determination of PAPP-A-/proMBP complex.

Outside pregnancy PAPP-A has been found to be secreted from a variety of cultured human cells such as fibroblasts, osteoblasts (15), ovarian granulosa cells (33), endometrial stromal cells (13) and coronary artery vascular smooth muscle cells (34). Furthermore, using immunohistochemistry and in situ hybridization, PAPP-A expression has been identified in vivo in ovary (35), in vascular plaques (20), and in healing human skin (36). However, it has only been demonstrated that PAPP-A isolated from human fibroblast-conditioned medium and from recombinant expression presents as a 400 kDa dimer (5,15).

PAPP-A, secreted by cells mentioned above in conditioned culture media, has been shown to have proteolytic activity. It seems likely that PAPP-A produced from all these in vitro sources exists as a dimer. However, to extrapolate the in vitro observation to in vivo situation is not justified. Having protease activity alone can not be used as the evidence that PAPP-A is present as a free form. In pregnancy, although over 99% of PAPP-A is present in the complex form, pregnancy serum and purified pregnancy PAPP-A have been shown to have protease activity (5,15,37). The reason for the measurable protease activity of pregnancy serum or pregnancy PAPP-A is attributed to the presence of less than 1% of an uninhibited PAPP-A dimer or perhaps from an incompletely inhibited 2:1 PAPP-A/proMBP complex (5).

During pregnancy, proMBP is synthesized in placental X cells, whereas PAPP-A is synthesized mainly in syncytiotrophoblasts (6). Therefore, the covalent PAPP-A/proMBP complex must form in the extracellular compartment after secretion. It is possible that PAPP-A protease activity is regulated by paracrine actions in the local environment (13). Outside pregnancy, proMBP has been demonstrated to present only in developing eosinophils rather than in mature eosinophils (38). But recently, proMBP immunoactivity was also detected in the estrogen-dominent follicular fluid from in vitro fertilization patients (33) and the origin of proMBP might relate to various ovarian cells (39). Moreover, it was reported that treatment of β-phorbol 12,13-didecanoate (β-PDD) induced proMBP expression from the cultured PAPP-A-producing human fibroblasts, leading to inhibition of the PAPP-A protease activity in cell conditioned medium (40), suggesting that PAPP-A protease activity may also be regulated in vivo by autocrine actions. But the question of why the complex structure is needed for proMBP's inhibitory effect is still unknown.

Previously atherosclerosis was viewed as a "plumbing" problem. But recent research has indicated that inflammation is pivotal in the development of arterial lesions (41). In comparison with stable plaques, disrupted plaques contain many inflammatory cells (42). PAPP-A has been shown to be present in unstable atherosclerotic plaques but absent in stable ones (20). Its expression can be significantly enhanced by cytokines such as TNFα from inflammatory cells (43). PAPP-A probably plays a crucial part in the inflammatory reactions in the atherosclerotic plaque, thus contributing to the progression of atherogenesis. Recently, we report that the cumulative risk of a primary cardiac end point is positively associated with the levels of circulating PAPP-A (23). The results support at least indirectly the view that PAPP-A (either alone or via IGFs) is a mediator of the adverse events that promote atherogenesis.

Our finding that ACS derived PAPP-A in circulation is not in complex with proMBP may have important clinical implications. In non-ACS individuals, variable levels of PAPP-A can be measured (22,26,44). The source of this immunoreactivity is not known, but may originate from seminal fluid, follicle fluid, corpus luteum, testes and other organs/tissues where PAPP-A expression has been reported (45). The PAPP-A concentrations determined for 80 non-ACS male subjects aged between 50 and 69 years varied from 1.51 to 7.59 mIU/L with a 97.5% upper reference limit of 5.68 mIU/L (22). The extent of increase in PAPP-A concentrations during ACS is widely variable but usually below 30 mIU/L (22,23). Using the upper reference limit as the decision limit means that a significant proportion of patients with ACS can be missed. We have previously reported (22) that the PAPP-A values in five out of fourteen MI patients were below the upper reference limit despite showing clear dynamic changes over time. Ideally, a decision limit not influenced by differences in the individual basal PAPP-A concentrations should be identified. Our preliminary observation shown here reveals that the basal PAPP-A values in absence of ACS are almost equally detected by the assay T for total PAPP-A and the assay C for PAPP-A in complex with proMBP, implying that the basal immunoreactivity of PAPP-A is caused by the PAPP-A/proMBP complex. Low levels (<4 mIU/L) of this complexed form of PAPP-A were also detected in the MI patients but exhibited no or little dynamic changes in the acute condition. Evidently, the form of PAPP-A associated with ACS is not in complex with proMBP. However, PAPP-A assays so far used in ACS measure total PAPP-A irrespective whether in complex with proMBP or not. This constitutes a major limitation of PAPP-A assessment in ACS. As already shown, one approach to determination of the ACS related PAPP-A is to calculate difference (delta value) between measured total PAPP-A and measured PAPP-A in complex with proMBP. The other viable option is to use assays preferably for free PAPP-A as illustrated in Table 1. We predict that immunoassays designed to measure the circulating form of PAPP-A specifically released from unstable atherosclerotic plaques is likely to improve the clinical specificity and sensitivity of PAPP-A when used as a cardiac risk marker.

In conclusion, our results provide the first evidence that circulating ACS related PAPP-A is different from circulating pregnancy related PAPP-A in that it is not complexed with proMBP. As early measurements of circulating PAPP-A may have diagnostic and prognostic value in patients who present with suspected ACS, these findings have important clinical implications for the design of assays to accurately measure atherosclerosis associated plasma protein A (AAPP-A) in the circulation.

It will be appreciated that the methods of the present invention can be incorporated in the form of a variety of embodiments, only a few of which are disclosed herein. It will be apparent for the expert skilled in the field that other embodiments exist and do not depart from the spirit of the invention. Thus, the described embodiments are illustrative and should not be construed as restrictive.

TABLE 1

Signal level differences in antibody combinations for measuring total PAPP-A, or PAPP-A in complex with proMBP or free PAPP-A

| | Antibody combination | Pregnancy derived PAPP-A Average counts (100 mIU/L, n = 3) | Atherosclerosis related PAPP-A Average counts (100 mIU/L, n = 3) |
|---|---|---|---|
| 1. | Combinations for total PAPP-A e.g. mab10E1/mab7A6* | 78718 | 78557 |
| 2. | Combinations for PAPP-A/proMBP e.g. mab10E1/mab8E8* | 25573 | 267 |
| 3. | Combinations preferably for free PAPP-A e.g. mab3C8/mab7A6* | 2372 | 40324 |

Note:
Asterisk indicates the antibody is in the europium-labeled form.

REFERENCES

1) Lin T M, Galbert S P, Kiefer D, Spellacy W N, Gall S. Characterization of four human pregnancy-associated plasma proteins. Am J Obstet Gynecol 1974; 118:223-236.
2) Folkersen J, Grudzinskas J G, Hindersson P, Teisner B, Westergaard J G. Pregnancy-associated plasma protein A: circulating levels during normal pregnancy. Am J Obstet Gynecol. 1981; 139:910-4.
3) Sinosich M J. Molecular characterization of pregnancy-associated plasma protein-A by electrophoresis. Electrophoresis. 1990 January; 11:70-8.
4) Oxvig C, Sand O, Kristensen T, Gleich G J, Sottrup-Jensen L. Circulating human pregnancy-associated plasma protein-A is disulfide-bridged to the proform of eosinophil major basic protein. J Biol Chem 1993; 268:12243-12246.
5) Overgaard M T, Haaning J, Boldt H B, Olsen I M, Laursen L S, Christiansen M, et al. Expression of recombinant human pregnancy-associated plasma protein-A and identification of the proform of eosinophil major basic protein as its physiological inhibitor. J Biol Chem 2000; 275: 31128-31133.
6) Bonno M, Oxvig C, Kephart G M, Wagner J M, Kristensen T, Sottrup-Jensen L, Gleich G J. Localization of pregnancy-associated plasma protein-A and colocalization of pregnancy-associated plasma protein-A messenger ribonucleic acid and eosinophil granule major basic protein messenger ribonucleic acid in placenta. Lab Invest. 1994; 71:560-6.
7) Kristensen T, Oxvig C, Sand O, Moller N P, Sottrup-Jensen L. Amino acid sequence of human pregnancy-associated plasma protein-A derived from cloned cDNA. Biochemistry 1994; 33:1592-1598.
8) Boldt H B, Overgaard M T, Laursen L S, Weyer K, Sottrup-Jensen L, Oxvig C. Mutational analysis of the proteolytic domain of pregnancy-associated plasma protein-A (PAPP-A): classification as a metzincin. Biochem J. 2001; 358: 359-67.
9) Barker R L, Gleich G J, Pease L R. Acidic precursor revealed in human eosinophil granule major basic protein cDNA. J Exp Med 1988; 168:1493-1498.
10) Wasmoen T L, Bell M P, Loegering D A, Gleich G J, Prendergast F G, McKean D J. Biochemical and amino acid sequence analysis of human eosinophil granule major basic protein. J Biol Chem 1988; 263:12559-12563.
11) Popken-Harris P, Checkel J, Loegering D, Madden B, Springett M, Kephart G, Gleich G J. Regulation and processing of a precursor form of eosinophil granule major basic protein (ProMBP) in differentiating eosinophils. Blood 1998; 92:623-631.
12) Gleich G J, Adolphson C R, Leiferman K M. The biology of the eosinophilic leukocyte. Annu Rev Med 1993; 44:85-101.
13) Giudice L C, Conover C A, Bale L, Faessen G H, Ilg K, Sun I, et al. Identification and regulation of the IGFBP-4 protease and its physiological inhibitor in human trophoblasts and endometrial stroma: evidence for paracrine regulation of IGF-II bioavailability in the placental bed during human implantation. J Clin Endocrinol Metab. 2002; 87:2359-66.
14) Oxvig C, Haaning J, Kristensen L, Wagner J M, Rubin I, Stigbrand T, Gleich G J, Sottrup-Jensen L. Identification of angiotensinogen and complement C3dg as novel proteins binding the proform of eosinophil major basic protein in human pregnancy serum and plasma J Biol Chem 1995; 270:13645-13651
15) Lawrence J B, Oxvig C, Overgaard M T, Sottrup-Jensen L, Gleich G J, Hays L G, et al. The insulin-like growth factor (IGF)-dependent IGF binding protein-4 protease secreted by human fibroblasts is pregnancy-associated plasma protein-A. Proc Natl Acad Sci USA 1999; 96:3149-3153.
16) Laursen L S, Overgaard M T, Soe R, Boldt H B, Sottrup-Jensen L, Giudice L C, et al. Pregnancy-associated plasma protein-A (PAPP-A) cleaves insulin-like growth factor binding protein (IGFBP)-5 independent of IGF: implications for the mechanism of IGFBP-4 proteolysis by PAPP-A. FEBS Lett 2001; 504:3640.
17) Hwa V, Oh Y, Rosenfeld R G. The insulin-like growth factor-binding protein (IGFBP) superfamily. Endocr Rev. 1999; 20:761-87.

18) Wald N, Stone R, Cuckle H S, Grudzinskas J G, Barkai G, Brambati B, Teisner B, Fuhrmann W. First trimester concentrations of pregnancy associated plasma protein A and placental protein 14 in Down's syndrome. BMJ. Jul. 4, 1992; 305:28.
19) Wapner R, Thom E, Simpson J L, Pergament E, Silver R, Filkins K, et al. First-trimester screening for trisomies 21 and 18. N Engl J Med. 2003; 349:1405-13.
20) Bayes-Genis A, Conover C A, Overgaard M T, Bailey K R, Christiansen M, Holmes D R Jr, et al. Pregnancy-associated plasma protein A as a marker of acute coronary syndromes. N Engl J Med. 2001; 345:1022-9.
21) Beaudeux J L, Burc L, Imbert-Bismut F, Giral P, Bernard M, Bruckert E, et al. Serum plasma pregnancy-associated protein A: a potential marker of echogenic carotid atherosclerotic plaques in asymptomatic hyperlipidemic subjects at high cardiovascular risk. Arterioscler Thromb Vasc Biol. 2003; 23: 7-10.
22) Qin Q P, Laitinen P, Majamaa-Voltti K, Eriksson S, Kumpula E K, Pettersson K. Release patterns of pregnancy associated plasma protein A (PAPP-A) in patients with acute coronary syndromes. Scand Cardiovasc J. 2002; 36:358-61.
23) Lund J, Qin Q P, Ilva T, Pettersson K, Voipio-Pulkki L M, Porela P, et al. Circulating pregnancy associated plasma protein A (PAPP-A) predicts outcome in patients with acute coronary syndromes but no Troponin I elevation. Circulation. 2003; 108:1924-6.
24) Bayes-Genis A, Conover C A, Schwartz R S. The insulin-like growth factor axis: A review of atherosclerosis and restenosis. Circ Res. 2000; 86:125-30.
25) Qin Q P, Christiansen M, Pettersson K. Point-of-care time-resolved immunofluorometric assay for human pregnancy-associated plasma protein A: use in first-trimester screening for Down syndrome. Clin Chem. 2002; 48:473-83.
26) Qin Q P, Christiansen M, Oxvig C, Pettersson K, Sottrup-Jensen L, Koch C, Norgaard-Pedersen B. Double-monoclonal immunofluorometric assays for pregnancy-associated plasma protein A/proeosinophil major basic protein (PAPP-A/proMBP) complex in first-trimester maternal serum screening for Down syndrome. Clin Chem. 1997; 43:2323-32.
27) Khosravi J, Diamandi A, Krishna R G, Bodani U, Mistry J, Khaja N. Pregnancy associated plasma protein-A: ultrasensitive immunoassay and determination in coronary heart disease. Clin Biochem. 2002; 35:531-8.
28) Pettersson K, Soderholm J R. Ultrasensitive two-site immunometric assay of human lutropin by time-resolved fluorometry. Clin Chem 1990; 36:1928-1933.
29) Takalo H, Mukkala V M, Mikola H, Liitti P, Hemmila I. Synthesis of europium(III) chelates suitable for labeling of bioactive molecules. Bioconj Chem 1994; 5:278-282.
30) Qin Q P, Lovgren T, Pettersson K. Development of highly fluorescent detection reagents for the construction of ultrasensitive immunoassays. Anal Chem. 2001; 73:1521-9.
31) Qin Q P. Maternal serum screening for Down syndrome in the first trimester with special emphasis on pregnancy associated plasma protein A [PhD thesis]. 1998:144 pp University of Turku Turku, Finland.
32) Overgaard M T, Sorensen E S, Stachowiak D, Boldt H B, Kristensen L, Sottrup-Jensen L, et al. Complex of pregnancy-associated plasma protein-A and the proform of eosinophil major basic protein. Disulfide structure and carbohydrate attachment. J Biol Chem. 2003; 278:2106-17
33) Conover C A, Faessen G F, Ilg K E, Chandrasekher Y A, Christiansen M, Overgaard M T, et al. Pregnancy-associated plasma protein-a is the insulin-like growth factor binding protein-4 protease secreted by human ovarian granulosa cells and is a marker of dominant follicle selection and the corpus luteum. Endocrinology. 2001; 142:2155.
34) Bayes-Genis A, Schwartz R S, Lewis D A, Overgaard M T, Christiansen M, Oxvig C, et al. Insulin-like growth factor binding protein-4 protease produced by smooth muscle cells increases in the coronary artery after angioplasty. Arterioscler Thromb Vasc Biol 2001; 21:335-341.
35) Hourvitz A, Widger A E, Filho F L, Chang R J, Adashi E Y, Erickson G F. Pregnancy-associated plasma protein-A gene expression in human ovaries is restricted to healthy follicles and corpora lutea J Clin Endocrinol Metab. 2000; 85:4916-20.
36) Chen B K, Leiferman K M, Pittelkow M R, Overgaard M T, Oxvig C, Conover C A. Localization and regulation of pregnancy-associated plasma protein a expression in healing human skin. J Clin Endocrinol Metab. 2003; 88:4465-71.
37) Qin X, Byun D, Lau K H, Baylink D J, Mohan S. Evidence that the interaction between insulin-like growth factor (IGF)-II and IGF binding protein (IGFBP)-4 is essential for the action of the IGF-II-dependent IGFBP-4 protease. Arch Biochem Biophys. 2000; 379:209-16.
38) Popken-Harris P, Checkel J, Loegering D, Madden B, Springett M, Kephart G, Gleich G J. Regulation and processing of a precursor form of eosinophil granule major basic protein (ProMBP) in differentiating eosinophils. Blood. 1998; 92:623-31.
39) Rhoton-Vlasak A, Gleich G J, Bischof P, Chegini N. Localization and cellular distribution of pregnancy-associated plasma protein-a and major basic protein in human ovary and corpora lutea throughout the menstrual cycle. Fertil Steril. 2003; 79:1149-53.
40) Chen B K, Overgaard M T, Bale L K, Resch Z T, Christiansen M, Oxvig C, Conover C A. Molecular regulation of the IGF-binding protein-4 protease system in human fibroblasts: identification of a novel inducible inhibitor. Endocrinology. 2002; 143:1199-205.
41) Libby P, Aikawa M. Stabilization of atherosclerotic plaques: new mechanisms and clinical targets. Nat Med. 2002, 8:1257-62.
42) Chyu K Y, Shah P K. The role of inflammation in plaque disruption and thrombosis. Rev Cardiovasc Med. 2001; 2:82-91.
43) Resch Z T, Chen B K, Bale L K, Oxvig C, Overgaard M T, Conover C A. Pregnancy-associated plasma protein A gene expression as a target of inflamatory cytokines. Endocrinology 2004; 145:1124-9.
44) Qin Q P, Nguyen T H, Christiansen M, Larsen S O, Norgaard-Pedersen B. Time-resolved immunofluorometric assay of pregnancy-associated plasma protein A in maternal serum screening for Down's syndrome in first trimester of pregnancy. Clin Chim Acta. 1996, 29; 254: 113-29.
45) Bischof P. Three pregnancy proteins (PP 12, PP 14, and PAPP-A): their biological and clinical relevance. Am J Perinatol 1989; 6:110-116.

The invention claimed is:

1. A bioaffinity assay for quantitative determination in a person's sample of free PAPP-A, defined as pregnancy associated plasma protein A (PAPP-A) that is not complexed to a proform of major basic protein (proMBP), wherein an amount of free PAPP-A present in said sample is determined either
    i) by exposing said sample to a first binder which binds total PAPP-A and to a second binder which is reactive with the proMBP subunit of the PAPP-A/proMBP-complex and detecting total PAPP-A bound to said first binder and detecting PAPP-A complexed to proMBP bound to said second binder in non-competitive sandwich assays, and calculating a difference between measured total PAPP-A and measured PAPP-A complexed to proMBP, or ii) by a direct bioaffinity assay measuring only free PAPP-A, by making PAPP-A complexed to proMBP non-capable of participating in a bioaffinity reaction in which said sample is exposed to a binder which binds total PAPP-A, by pre-absorbing PAPP-A complexed to proMBP by the steps of exposing said sample to a first binder which binds to proMBP, allowing said proMBP to bind to said first binder, absorbing said first binder onto a solid phase and separating said first binder and said bound proMBP from said sample, exposing said sample, from which proMBP has been separated, to a second binder which binds total PAPP-A, and detecting the bound PAPP-A, wherein said first binder and said second binder in i) and ii) are both independently either an antibody or antibody fragment.

2. The assay according to claim 1, wherein free PAPP-A is determined according to alternative i) and two assays are performed, in which one aliquot of the sample is exposed to a first binder which binds total PAPP-A and the total PAPP-A bound to the first binder is detected, and another aliquot of said sample is exposed to a second binder which is reactive with the proMBP subunit of the PAPP-A/proMBP complex and the PAPP-A complexed to proMBP bound to the second binder is detected, and the amount of free PAPP-A is calculated as a difference between determined total PAPP-A and PAPP-A complexed to proMBP.

3. The assay according to claim 1, wherein in alternative i) the first and second binders are capture binders.

4. The assay according to claim 1, wherein in alternative i) the first and second binders are labelled binders.

5. The assay according to claim 1, wherein free PAPP-A is determined according to alternative i) as one single dual analyte assay where the sample is exposed to a capture binder, which binds total PAPP-A, and to two detecting binders labelled with different labels, so that a first detecting binder labeled with a first label is directed to an epitope present in any PAPP-A molecule, where a signal of the first label is detected to give total PAPP-A, and a second detecting binder labeled with a second label is directed to an epitope in a proMBP subunit complexed to PAPP-A, where a signal of the second label is detected to give PAPP-A complexed to proMBP.

6. A method for diagnosing persons suffering from an acute coronary syndrome or persons at risk of acute coronary syndrome, comprising comparing a value of a marker present in a sample derived from said person to a reference value for said marker, diagnosing whether said person is at risk of acute coronary syndrome based on said comparison, wherein said marker either consists of free PAPP-A, defined as pregnancy associated plasma protein A (PAPP-A) which is not complexed to a proform of major basic protein (proMBP), as such, or said marker consists of a ratio selected from the group consisting of free PAPP-A/total PAPP-A, free PAPP-A/PAPP-A complexed to proMBP, and PAPP-A complexed to proMBP/total PAPP-A, wherein free PAPP-A is determined by a bioaffinity assay method for quantitative determination in a sample of free PAPP-A, either i) as a calculated difference between measured total PAPP-A and measured PAPP-A complexed to proMBP, either a) in a method wherein two assay methods are performed, in which one aliquot of the sample is exposed to a first binder which binds total PAPP-A and said total PAPP-A bound to said first binder is detected in a non-competitive sandwich assay, and another aliquot of sample is exposed to a second binder which is reactive with the proMBP subunit of the PAPP-A/proMBP complex and said PAPP-A complexed to proMBP bound to said second binder is detected in a non-competitive sandwich assay, and the amount of free PAPP-A is calculated as a difference between determined total PAPP-A and PAPP-A complexed to proMBP, or b) in a method wherein free PAPP-A is determined as one single dual analyte assay where the sample is exposed to a capture binder, which binds total PAPP-A, and to two detecting binders labeled with different labels, so that a first detecting binder labeled with a first label is directed to an epitope present in any PAPP-A molecule, where a signal of the first label is detected to give total PAPP-A, and a second detecting binder labeled with a second label is directed to an epitope in a proMBP subunit complexed to PAPP-A, where a signal of the second label is detected to give PAPP-A complexed to proMBP, or ii) by a direct bioaffinity assay measuring only free PAPP-A, by making PAPP-A complexed to proMBP non-capable of participating in a bioaffinity reaction in which said sample is exposed to a binder which binds total PAPP-A, by pre-absorbing PAPP-A complexed to proMBP by the steps of exposing said sample to a first binder which binds to proMBP, allowing said proMBP to bind to said first binder, absorbing said first binder onto a solid phase and separating said first binder and said bound proMBP from said sample, exposing said sample, from which proMBP has been separated, to a second binder which binds total PAPP-A, and detecting the bound PAPP-A, wherein said first binder and said second binder are both independently either an antibody or antibody fragment.

* * * * *